US007279321B2

(12) United States Patent
Sariaslani et al.

(10) Patent No.: US 7,279,321 B2
(45) Date of Patent: Oct. 9, 2007

(54) METHODS FOR INCREASING THE RESISTANCE OF A HOST CELL TO AROMATIC CARBOXYLIC ACIDS

(75) Inventors: Fateme Sima Sariaslani, Wilmington, DE (US); Tina K. Van Dyk, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 144 days.

(21) Appl. No.: 10/759,898

(22) Filed: Jan. 16, 2004

(65) Prior Publication Data

US 2004/0147000 A1 Jul. 29, 2004

Related U.S. Application Data

(60) Provisional application No. 60/440,760, filed on Jan. 17, 2003.

(51) Int. Cl.
*C12N 1/20* (2006.01)
*C12N 15/00* (2006.01)
*C12N 15/74* (2006.01)
*C07K 1/00* (2006.01)
*C07H 21/04* (2006.01)

(52) U.S. Cl. ............................ 435/252.3; 435/252.33; 435/320.1; 435/471; 530/350; 536/23.1

(58) Field of Classification Search ............ 435/252.3, 435/252.33, 320.1, 471; 530/350; 536/23.1
See application file for complete search history.

(56) References Cited

U.S. PATENT DOCUMENTS

| | | | |
|---|---|---|---|
| 5,292,643 | A | 3/1994 | Shibano et al. |
| 6,225,089 | B1 | 5/2001 | Chen |
| 6,235,882 | B1 | 5/2001 | Chen |
| 6,368,837 | B1 | 4/2002 | Gatenby et al. |
| 6,521,748 | B2 | 2/2003 | Tang |

OTHER PUBLICATIONS

Welch et al. Accession NP-756937. Dec. 2, 2005.*
U.S. Appl. No. 10/439,479, Dupont Natl Appl.
U.S. Appl. No. 60/440,965, Dupont Prv. Appl.
Saier et al. Evoluntionary origins of multidrug and drug-specific efflux pumps in bacteria, FASEB J. 12: pp. 265-274, 1998.
Jack et al., The drug/metabolite transporter superfamily, Eur. J. Biochem.268: pp. 3620-3639, 2001.
Li et al., Role of the Multidrug Efflux Systems of *Pseudomonas aeruginosa* in Organic Solvent Tolerance, J. Bacteriol. 180: pp. 2987-2991, 1998.
Ramos et al., Efflux Pumps Involved in Toluene Tolerance in *Pseudomonas putida* TOT-T1E J. Bacteriol. 180: pp. 3323-3329, 1998.
Godoy et al.,Involvement of the TonB System in Tolerance to Solvents and Drugs in *Pseudomonas putida* DOT-T1E, J. Bacteriol. 183: 5285-5292, 2001.
Ramos-Gonzalez et al., Physiological Characterization of *Pseudomonas putida* DOT-T1E Tolerance to p-Hydroxybenzoate, Appl. Environ. Microbiol. 67: pp. 4338-4341, 2001.
Ditty and Harwood, Conserved Cytoplasmic Loops Are Important for both the Transport and Chemotaxis Functions of PcaK, a Protein from *Pseudomonas putida* with 12 Membrane-Spanning Regions, J. Bacteriol. 181: pp. 5068-5074, 1999.
Paulsen et al., A family of Gram-negative bacterial outer membrane factors that function in the export of proteins, carbohydrates, drugs and heavy metals form Gram-negative bacteria, FEMS Microbiol. Lett. 156: pp. 1-8, 1997.
Harley and Saier, A Novel Ubiquitous Family of Putative Efflux Transporters, J. Mol. Microbiol. Biotechnol. 2: pp. 195-198, 2000.
Ramos et al., Mechanisms of solvent tolerance in gram-negative bacteria, Annual Review of Microbiology, vol. 56, 2002, pp. 743-768.

* cited by examiner

*Primary Examiner*—Ponnathapu Achutamurthy
*Assistant Examiner*—Christian L. Fronda

(57) ABSTRACT

The invention provides methods of increasing the production of aromatic carboxylic acids from a host cell via manipulation of the yhcRQP operon encoding a family of efflux proteins. Up-regulation of all or a sub-set of the genes in the yhcRQP were additionally found to enhance tolerance to aromatic carboxylic acids toxicity.

9 Claims, No Drawings

SEQUENCE LISTING

<160> NUMBER OF SEQ ID NOS: 21

<210> SEQ ID NO 1
<211> LENGTH: 1968
<212> TYPE: DNA
<213> ORGANISM: Escherichia coli

<400> SEQUENCE: 1
atgggtattt tctccattgc taaccaacat attcgctttg cggtaaaact ggcgaccgcc 60
attgtactgg cgctgtttgt tggctttcac ttccagctgg aaacgccacg ctgggcggta 120
ctgacagcgg cgattgttgc cgccggtacg gcctttgctg cgggaggtga accgtattct 180
ggcgctattc gctatcgtgg ctttttgcgc atcatcggca catttattgg ctgtattgcc 240
ggactggtga tcatcattgc gatgatccgc gcaccattat tgatgattct ggtgtgctgt 300
atctgggccg gtttttgtac ctggatatcc tcgctggtac gaatagaaaa ctcgtatgcg 360
tgggggctgg ccggttatac cgcgctgatc attgtgatca ccattcagcc ggaaccattg 420
cttacgccgc agtttgccgt cgaacgttgt agcgagatcg ttatcggtat tgtgtgtgcg 480
attatggcgg atttgctctt ttctccgcga tcgatcaaac aagaagtgga tcgagagctg 540
gaaagtttgc tggtcgcgca atatcaatta atgcaactct gtatcaagca tggcgatggt 600
gaagttgtcg ataaagcctg ggcgacctg gtgcgacgca ccacggcgct acaaggcatg 660
cgcagcaacc tgaatatgga atcttcccgc tgggcgcggg ccaatcgacg tttaaaagcg 720
atcaatacgc tatcgctgac gctgattacc caatcctgcg aaacttatct tattcagaat 780
acgcgcccgg aattgatcac tgatactttc cgcgaatttt ttgacacgcc ggtagaaacc 840
gcgcaggacg tccacaagca gctcaaacgc ctgcggagag ttatcgcctg gaccggggaa 900
cgggaaacgc ctgtcaccat ttatagctgg gtcgcggcgg caacgcgtta tcagcttctc 960
aagcgcggcg ttatcagtaa cacaaaaatc aacgccaccg aagaagagat cctgcaaggc 1020
gaaccggaag taaaagtaga gtcagccgaa cgtcatcatg caatggttaa cttctggcga 1080
accacacttt cctgcattct gggcacgctt ttctggctgt ggacgggctg gacttccggc 1140
agtggtgcaa tggtgatgat tgcggtagtg acgtcactgg caatgcgttt gccgaatcca 1200
cgcatggtgg cgatcgactt tatctacggg acgctggccg cgctgccgtt agggctgctc 1260
tactttttgg tgattatccc taatacccaa cagagcatgt tgctgctgtg cattagcctg 1320
gcagtgctgg gattcttcct cggtatagaa gtacagaaac ggcgactggg ctcgatgggg 1380
gcactggcca gcaccataaa tattatcgtg ctggataacc cgatgacttt ccatttcagt 1440
cagtttctcg acagcgcatt agggcaaatc gtcggctgtg tgctcgcgtt caccgttatt 1500
ttgctggtgc gggataaatc gcgcgacagg accggacgtg tactgcttaa tcagtttgtt 1560
tctgccgctg tttccgcgat gactaccaat gtggcacgtc gtaaagagaa ccacctcccg 1620
gcactttatc agcagctgtt tttgctgatg aataagttcc caggggattt gccgaaattt 1680
cgcctggcgc tgacgatgat tatcgcgcac cagcgcctgc gtgatgcacc gatcccggtt 1740

-continued

```
aacgaggatt tatcggcgtt tcaccgacaa atgcgccgca cagcagacca tgtgatatct   1800

gcccgtagcg atgataaacg tcgtcggtac tttggccagt tgctggaaga actggaaatc   1860

taccaggaaa agctacgcat ctggcaagcg ccaccgcagg tgacggaacc ggtaaatcgg   1920

ctggcgggga tgctccataa gtatcaacat gcgttgaccg atagttaa                1968
```

<210> SEQ ID NO 2
<211> LENGTH: 933
<212> TYPE: DNA
<213> ORGANISM: Escherichia coli

<400> SEQUENCE: 2

```
gtgaaaacac taataagaaa attctcccgt acggccatca cggtcgtatt agtcattctg     60

gccttcatcg caatttttaa tgcctgggtc tattacaccg aatcccccctg gacgcgtgac   120

gcgcgcttta gcgctgacgt cgttgcgatc gcgccggacg tttctggact cattacccag    180

gtgaatgttc atgataacca gctggtgaaa aaaggacaga tactgttcac catcgaccag    240

ccgcgctatc aaaaggcgct tgaggaagcg caagccgatg ttgcttatta tcaggtactg    300

gcacaggaga aacgccagga ggccggacgt cgtaaccgtc tcggtgtgca ggcgatgtct    360

cgcgaagaga tcgaccaggc caacaacgta ctacaaacgg ttctgcatca gttagcgaaa    420

gcgcaggcga cccgcgatct ggcaaaactg gatcttgaac gcacggtgat ccgcgcgcca    480

gcagatggct gggtgaccaa cctcaacgtc tataccggtg agtttattac tcgaggatca    540

acggcggttg cgctggtgaa acagaactcc ttctatgtac tggcctatat ggaagaaact    600

aagctggaag gggtgcgtcc ggggtatcgt gcagagatca cgccgcttgg cagtaacaaa    660

gtgctgaaag ggactgttga tagtgttgcc gcaggggtca ccaacgccag cagcacgcgt    720

gacgacaaag ggatggcgac tatagactct aaccttgaat gggtgcgtct tgcgcaacgt    780

gttccggttc gtattcgtct cgacaaccag caagagaaca tctggcctgc gggcaccact    840

gctacagtgg tggtcactgg caaacaagat cgcgacgaaa gccaggattc gttcttccgt    900

aaaatggccc atcgcctgcg tgagtttggt taa                                 933
```

<210> SEQ ID NO 3
<211> LENGTH: 2906
<212> TYPE: DNA
<213> ORGANISM: Escherichia coli

<400> SEQUENCE: 3

```
gtgaaaacac taataagaaa attctcccgt acggccatca cggtcgtatt agtcattctg     60

gccttcatcg caatttttaa tgcctgggtc tattacaccg aatcccccctg gacgcgtgac   120

gcgcgcttta gcgctgacgt cgttgcgatc gcgccggacg tttctggact cattacccag    180

gtgaatgttc atgataacca gctggtgaaa aaaggacaga tactgttcac catcgaccag    240

ccgcgctatc aaaaggcgct tgaggaagcg caagccgatg ttgcttatta tcaggtactg    300

gcacaggaga aacgccagga ggccggacgt cgtaaccgtc tcggtgtgca ggcgatgtct    360

cgcgaagaga tcgaccaggc caacaacgta ctacaaacgg ttctgcatca gttagcgaaa    420

gcgcaggcga cccgcgatct ggcaaaactg gatcttgaac gcacggtgat ccgcgcgcca    480

gcagatggct gggtgaccaa cctcaacgtc tataccggtg agtttattac tcgaggatca    540

acggcggttg cgctggtgaa acagaactcc ttctatgtac tggcctatat ggaagaaact    600

aagctggaag gggtgcgtcc ggggtatcgt gcagagatca cgccgcttgg cagtaacaaa    660

gtgctgaaag ggactgttga tagtgttgcc gcaggggtca ccaacgccag cagcacgcgt    720
```

-continued

```
gacgacaaag ggatggcgac tatagactct aaccttgaat gggtgcgtct tgcgcaacgt    780
gttccggttc gtattcgtct cgacaaccag caagagaaca tctggcctgc gggcaccact    840
gctacagtgg tggtcactgg caaacaagat cgcgacgaaa gccaggattc gttcttccgt    900
aaaatggccc atcgcctgcg tgagtttggt taatcacgat gggtattttc tccattgcta    960
accaacatat tcgctttgcg gtaaaactgg cgaccgccat tgtactggcg ctgtttgttg   1020
gctttcactt ccagctggaa acgccacgct gggcggtact gacagcggcg attgttgccg   1080
ccggtacggc ctttgctgcg ggaggtgaac cgtattctgg cgctattcgc tatcgtggct   1140
ttttgcgcat catcggcaca tttattggct gtattgccgg actggtgatc atcattgcga   1200
tgatccgcgc accattattg atgattctgg tgtgctgtat ctgggccggt ttttgtacct   1260
ggatatcctc gctggtacga atagaaaact cgtatgcgtg gggctggcc ggttataccg    1320
cgctgatcat tgtgatcacc attcagccgg aaccattgct tacgccgcag tttgccgtcg   1380
aacgttgtag cgagatcgtt atcggtattg tgtgtgcgat tatggcggat ttgctctttt   1440
ctccgcgatc gatcaaacaa gaagtggatc gagagctgga aagtttgctg gtcgcgcaat   1500
atcaattaat gcaactctgt atcaagcatg gcgatggtga agttgtcgat aaagcctggg   1560
gcgacctggt gcgacgcacc acggcgctac aaggcatgcg cagcaacctg aatatggaat   1620
cttcccgctg ggcgcgggcc aatcgacgtt taaaagcgat caatacgcta tcgctgacgc   1680
tgattaccca atcctgcgaa acttatctta ttcagaatac gcgcccggaa ttgatcactg   1740
atactttccg cgaatttttt gacacgccgg tagaaaccgc gcaggacgtc cacaagcagc   1800
tcaaacgcct gcggagagtt atcgcctgga ccggggaacg ggaaacgcct gtcaccattt   1860
atagctgggt cgcggcggca acgcgttatc agcttctcaa gcgcggcgtt atcagtaaca   1920
caaaaatcaa cgccaccgaa gaagagatcc tgcaaggcga accggaagta aaagtagagt   1980
cagccgaacg tcatcatgca atggttaact tctggcgaac cacactttcc tgcattctgg   2040
gcacgctttt ctggctgtgg acgggctgga cttccggcag tggtgcaatg gtgatgattg   2100
cggtagtgac gtcactggca atgcgtttgc cgaatccacg catggtggcg atcgacttta   2160
tctacgggac gctggccgcg ctgccgttag ggctgctcta ctttttggtg attatcccta   2220
atacccaaca gagcatgttg ctgctgtgca ttagcctggc agtgctggga ttcttcctcg   2280
gtatagaagt acagaaacgg cgactgggct cgatgggggc actggccagc accataaata   2340
ttatcgtgct ggataacccg atgactttcc atttcagtca gtttctcgac agcgcattag   2400
ggcaaatcgt cggctgtgtg ctcgcgttca ccgttatttt gctggtgcgg gataaatcgc   2460
gcgacaggac cggacgtgta ctgcttaatc agtttgtttc tgccgctgtt tccgcgatga   2520
ctaccaatgt ggcacgtcgt aaagagaacc acctcccggc actttatcag cagctgtttt   2580
tgctgatgaa taagttccca ggggatttgc cgaaatttcg cctggcgctg acgatgatta   2640
tcgcgcacca gcgcctgcgt gatgcaccga tcccggttaa cgaggattta tcggcgtttc   2700
accgacaaat gcgccgcaca gcagaccatg tgatatctgc ccgtagcgat gataaacgtc   2760
gtcggtactt tggccagttg ctggaagaac tggaaatcta ccaggaaaag ctacgcatct   2820
ggcaagcgcc accgcaggtg acggaaccgg taaatcggct ggcggggatg ctccataagt   2880
atcaacatgc gttgaccgat agttaa                                        2906
```

<210> SEQ ID NO 4
<211> LENGTH: 3186
<212> TYPE: DNA

-continued

<213> ORGANISM: Escherichia coli

<400> SEQUENCE: 4
atgcccttct ctgcggcgac agatgctgaa aataataacg cctgctctct ctttacaacc 60
aaggtcaaca tgagtctgtt tcccgttatc gtggtgtttg ggctgtcctt cccaccgata 120
ttttttgaat tgcttttatc actggcgatt ttctggctgg tgcgccgggt acttgtgcca 180
acaggtatct acgactttgt ctggcatccg gcgttgttca acaccgcgct ctattgctgc 240
ttgttttatt tgatatcgcg actgttcgtt tgaggttgaa gtgaaaacac taataagaaa 300
attctcccgt acggccatca cggtcgtatt agtcattctg gccttcatcg caatttttaa 360
tgcctgggtc tattacaccg aatccccctg gacgcgtgac gcgcgcttta gcgctgacgt 420
cgttgcgatc gcgccggacg tttctggact cattacccag gtgaatgttc atgataacca 480
gctggtgaaa aaaggacaga tactgttcac catcgaccag ccgcgctatc aaaaggcgct 540
tgaggaagcg caagccgatg ttgcttatta tcaggtactg gcacaggaga aacgccagga 600
ggccggacgt cgtaaccgtc tcggtgtgca ggcgatgtct cgcgaagaga tcgaccaggc 660
caacaacgta ctacaaacgg ttctgcatca gttagcgaaa gcgcaggcga cccgcgatct 720
ggcaaaactg gatcttgaac gcacggtgat ccgcgcgcca gcagatggct gggtgaccaa 780
cctcaacgtc tataccggtg agtttattac tcgaggatca acggcggttg cgctggtgaa 840
acagaactcc ttctatgtac tggcctatat ggaagaaact aagctggaag gggtgcgtcc 900
ggggtatcgt gcagagatca cgccgcttgg cagtaacaaa gtgctgaaag ggactgttga 960
tagtgttgcc gcaggggtca ccaacgccag cagcacgcgt gacgacaaag ggatggcgac 1020
tatagactct aaccttgaat gggtgcgtct tgcgcaacgt gttccggttc gtattcgtct 1080
cgacaaccag caagagaaca tctggcctgc gggcaccact gctacagtgg tggtcactgg 1140
caaacaagat cgcgacgaaa gccaggattc gttcttccgt aaaatggccc atcgcctgcg 1200
tgagtttggt taatcacgat gggtattttc tccattgcta accaacatat tcgctttgcg 1260
gtaaaactgg cgaccgccat tgtactggcg ctgtttgttg gctttcactt ccagctggaa 1320
acgccacgct gggcggtact gacagcggcg attgttgccg ccggtacggc ctttgctgcg 1380
ggaggtgaac cgtattctgg cgctattcgc tatcgtggct ttttgcgcat catcggcaca 1440
tttattggct gtattgccgg actggtgatc atcattgcga tgatccgcgc accattattg 1500
atgattctgg tgtgctgtat ctgggccggt ttttgtacct ggatatcctc gctggtacga 1560
atagaaaact cgtatgcgtg gggctggcc ggttataccg cgctgatcat tgtgatcacc 1620
attcagccgg aaccattgct tacgccgcag tttgccgtcg aacgttgtag cgagatcgtt 1680
atcggtattg tgtgtgcgat tatggcggat ttgctctttt ctccgcgatc gatcaaacaa 1740
gaagtggatc gagagctgga aagtttgctg gtcgcgcaat atcaattaat gcaactctgt 1800
atcaagcatg gcgatggtga agttgtcgat aaagcctggg gcgacctggt gcgacgcacc 1860
acggcgctac aaggcatgcg cagcaacctg aatatggaat cttcccgctg ggcgcgggcc 1920
aatcgacgtt taaaagcgat caatacgcta tcgctgacgc tgattaccca atcctgcgaa 1980
acttatctta ttcagaatac gcgcccggaa ttgatcactg atactttccg cgaatttttt 2040
gacacgccgg tagaaaccgc gcaggacgtc cacaagcagc tcaaacgcct gcggagagtt 2100
atcgcctgga ccggggaacg ggaaacgcct gtcaccattt atagctgggt cgcggcggca 2160
acgcgttatc agcttctcaa gcgcggcgtt atcagtaaca caaaaatcaa cgccaccgaa 2220
gaagagatcc tgcaaggcga accggaagta aaagtagagt cagccgaacg tcatcatgca 2280

-continued

```
atggttaact tctggcgaac cacactttcc tgcattctgg gcacgctttt ctggctgtgg   2340
acgggctgga cttccggcag tggtgcaatg gtgatgattg cggtagtgac gtcactggca   2400
atgcgtttgc cgaatccacg catggtggcg atcgacttta tctacgggac gctggccgcg   2460
ctgccgttag ggctgctcta ctttttggtg attatcccta atacccaaca gagcatgttg   2520
ctgctgtgca ttagcctggc agtgctggga ttcttcctcg gtatagaagt acagaaacgg   2580
cgactgggct cgatgggggc actggccagc accataaata ttatcgtgct ggataacccg   2640
atgactttcc atttcagtca gtttctcgac agcgcattag ggcaaatcgt cggctgtgtg   2700
ctcgcgttca ccgttatttt gctggtgcgg gataaatcgc gcgacaggac cggacgtgta   2760
ctgcttaatc agtttgtttc tgccgctgtt tccgcgatga ctaccaatgt ggcacgtcgt   2820
aaagagaacc acctcccggc actttatcag cagctgtttt tgctgatgaa taagttccca   2880
ggggatttgc cgaaatttcg cctggcgctg acgatgatta tcgcgcacca gcgcctgcgt   2940
gatgcaccga tcccggttaa cgaggattta tcggcgtttc accgacaaat gcgccgcaca   3000
gcagaccatg tgatatctgc ccgtagcgat gataaacgtc gtcggtactt tggccagttg   3060
ctggaagaac tggaaatcta ccaggaaaag ctacgcatct ggcaagcgcc accgcaggtg   3120
acggaaccgg taaatcggct ggcggggatg ctccataagt atcaacatgc gttgaccgat   3180
agttaa                                                              3186
```

```
<210> SEQ ID NO 5
<211> LENGTH: 655
<212> TYPE: PRT
<213> ORGANISM: Escherichia coli

<400> SEQUENCE: 5

Met Gly Ile Phe Ser Ile Ala Asn Gln His Ile Arg Phe Ala Val Lys
1               5                   10                  15

Leu Ala Thr Ala Ile Val Leu Ala Leu Phe Val Gly Phe His Phe Gln
            20                  25                  30

Leu Glu Thr Pro Arg Trp Ala Val Leu Thr Ala Ala Ile Val Ala Ala
        35                  40                  45

Gly Thr Ala Phe Ala Ala Gly Gly Glu Pro Tyr Ser Gly Ala Ile Arg
    50                  55                  60

Tyr Arg Gly Phe Leu Arg Ile Ile Gly Thr Phe Ile Gly Cys Ile Ala
65                  70                  75                  80

Gly Leu Val Ile Ile Ile Ala Met Ile Arg Ala Pro Leu Leu Met Ile
                85                  90                  95

Leu Val Cys Cys Ile Trp Ala Gly Phe Cys Thr Trp Ile Ser Ser Leu
            100                 105                 110

Val Arg Ile Glu Asn Ser Tyr Ala Trp Gly Leu Ala Gly Tyr Thr Ala
        115                 120                 125

Leu Ile Ile Val Ile Thr Ile Gln Pro Glu Pro Leu Leu Thr Pro Gln
    130                 135                 140

Phe Ala Val Glu Arg Cys Ser Glu Ile Val Ile Gly Ile Val Cys Ala
145                 150                 155                 160

Ile Met Ala Asp Leu Leu Phe Ser Pro Arg Ser Ile Lys Gln Glu Val
                165                 170                 175

Asp Arg Glu Leu Glu Ser Leu Leu Val Ala Gln Tyr Gln Leu Met Gln
            180                 185                 190

Leu Cys Ile Lys His Gly Asp Gly Glu Val Val Asp Lys Ala Trp Gly
        195                 200                 205
```

-continued

```
Asp Leu Val Arg Arg Thr Thr Ala Leu Gln Gly Met Arg Ser Asn Leu
    210                 215                 220

Asn Met Glu Ser Ser Arg Trp Ala Arg Ala Asn Arg Arg Leu Lys Ala
225                 230                 235                 240

Ile Asn Thr Leu Ser Leu Thr Leu Ile Thr Gln Ser Cys Glu Thr Tyr
                245                 250                 255

Leu Ile Gln Asn Thr Arg Pro Glu Leu Ile Thr Asp Thr Phe Arg Glu
            260                 265                 270

Phe Phe Asp Thr Pro Val Glu Thr Ala Gln Asp Val His Lys Gln Leu
        275                 280                 285

Lys Arg Leu Arg Arg Val Ile Ala Trp Thr Gly Glu Arg Glu Thr Pro
    290                 295                 300

Val Thr Ile Tyr Ser Trp Val Ala Ala Ala Thr Arg Tyr Gln Leu Leu
305                 310                 315                 320

Lys Arg Gly Val Ile Ser Asn Thr Lys Ile Asn Ala Thr Glu Glu Glu
                325                 330                 335

Ile Leu Gln Gly Glu Pro Glu Val Lys Val Glu Ser Ala Glu Arg His
            340                 345                 350

His Ala Met Val Asn Phe Trp Arg Thr Thr Leu Ser Cys Ile Leu Gly
        355                 360                 365

Thr Leu Phe Trp Leu Trp Thr Gly Trp Thr Ser Gly Ser Gly Ala Met
    370                 375                 380

Val Met Ile Ala Val Val Thr Ser Leu Ala Met Arg Leu Pro Asn Pro
385                 390                 395                 400

Arg Met Val Ala Ile Asp Phe Ile Tyr Gly Thr Leu Ala Ala Leu Pro
                405                 410                 415

Leu Gly Leu Leu Tyr Phe Leu Val Ile Ile Pro Asn Thr Gln Gln Ser
            420                 425                 430

Met Leu Leu Leu Cys Ile Ser Leu Ala Val Leu Gly Phe Phe Leu Gly
        435                 440                 445

Ile Glu Val Gln Lys Arg Arg Leu Gly Ser Met Gly Ala Leu Ala Ser
    450                 455                 460

Thr Ile Asn Ile Ile Val Leu Asp Asn Pro Met Thr Phe His Phe Ser
465                 470                 475                 480

Gln Phe Leu Asp Ser Ala Leu Gly Gln Ile Val Gly Cys Val Leu Ala
                485                 490                 495

Phe Thr Val Ile Leu Leu Val Arg Asp Lys Ser Arg Asp Arg Thr Gly
            500                 505                 510

Arg Val Leu Leu Asn Gln Phe Val Ser Ala Ala Val Ser Ala Met Thr
        515                 520                 525

Thr Asn Val Ala Arg Arg Lys Glu Asn His Leu Pro Ala Leu Tyr Gln
    530                 535                 540

Gln Leu Phe Leu Leu Met Asn Lys Phe Pro Gly Asp Leu Pro Lys Phe
545                 550                 555                 560

Arg Leu Ala Leu Thr Met Ile Ile Ala His Gln Arg Leu Arg Asp Ala
                565                 570                 575

Pro Ile Pro Val Asn Glu Asp Leu Ser Ala Phe His Arg Gln Met Arg
            580                 585                 590

Arg Thr Ala Asp His Val Ile Ser Ala Arg Ser Asp Asp Lys Arg Arg
        595                 600                 605

Arg Tyr Phe Gly Gln Leu Leu Glu Glu Leu Glu Ile Tyr Gln Glu Lys
    610                 615                 620
```

-continued

```
Leu Arg Ile Trp Gln Ala Pro Pro Gln Val Thr Glu Pro Val Asn Arg
625                 630                 635                 640

Leu Ala Gly Met Leu His Lys Tyr Gln His Ala Leu Thr Asp Ser
                645                 650                 655
```

<210> SEQ ID NO 6
<211> LENGTH: 36
<212> TYPE: DNA
<213> ORGANISM: Artificial Sequence
<220> FEATURE:
<223> OTHER INFORMATION: Primer

<400> SEQUENCE: 6
gaagttagca agcttttaac tatcggtcaa cgcatg 36

<210> SEQ ID NO 7
<211> LENGTH: 36
<212> TYPE: DNA
<213> ORGANISM: Artificial Sequence
<220> FEATURE:
<223> OTHER INFORMATION: Primer

<400> SEQUENCE: 7
acaggagaat gaattcatgc ccttctctgc ggcgac 36

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
ttaactatcg gtcaacgcat gtt 23

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
acaggagaat gaattcgtga aaacactaat aagaaa 36

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ttaaccaaac tcacgcaggc 20

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
acaggagaat gaattcatgc ccttctctgc ggcgac 36

-continued

<210> SEQ ID NO 12
<211> LENGTH: 32
<212> TYPE: DNA
<213> ORGANISM: Artificial Sequence
<220> FEATURE:
<223> OTHER INFORMATION: Primer

<400> SEQUENCE: 12
gttagcaagc ttttaactat cggtcaacgc at 32

<210> SEQ ID NO 13
<211> LENGTH: 32
<212> TYPE: DNA
<213> ORGANISM: Artificial Sequence
<220> FEATURE:
<223> OTHER INFORMATION: Primer

<400> SEQUENCE: 13
agcagtgaat tcatgggtat tttctccatt gc 32

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
gacggcggct ttgttgaata aatc 24

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
ttggaattta atcgcggcct cgagc 25

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tgtttgatcg atcgcggaga 20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tcggcacatt tattggctgt 20

<210> SEQ ID NO 18
<211> LENGTH: 25
<212> TYPE: DNA
<213> ORGANISM: Artificial Sequence
<220> FEATURE:
<223> OTHER INFORMATION: Primer

```
-continued

<400> SEQUENCE: 18

acctacaaca aagctctcat caacc                                          25

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19

gcaatgtaac atcagagatt ttgag                                          25

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20

aacgcatgtc ggtgtttgcc                                                20

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21

cgtgcatctc ctgaacaatt taccg                                          25
```

METHODS FOR INCREASING THE RESISTANCE OF A HOST CELL TO AROMATIC CARBOXYLIC ACIDS

This application claims the benefit of U.S. Provisional Application 60/440,760, filed Jan. 17, 2003.

FIELD OF INVENTION

The present invention relates to the fields of molecular biology and microbiology. More specifically, this invention pertains to novel genes encoding members of the putative efflux transporter (PET) family of efflux proteins for aromatic carboxylic acids.

BACKGROUND

Various naturally occurring aromatic carboxylic acids have been found to have utility in industrial applications. Compounds such as para-hydroxycinnamic acid (PHCA) and para-hydroxybenzoic acid (PHBA) are high-value, compounds that may be used as monomers for the production of Liquid Crystal Polymers (LCP). LCPs are polymers that exhibit an intermediate or mesophase between the glass-transition temperature and the transition temperature to the isotropic liquid or have at least one mesophase for certain ranges of concentration and temperature. The molecules in these mesophases behave like liquids and flow, but also exhibit the anisotropic properties of crystals. LCPs are used in liquid crystal displays, and in high speed connectors and flexible circuits for electronic, telecommunication, and aerospace applications. Because of their resistance to sterilizing radiation and their high oxygen and water vapor barrier properties, LCPs are used in medical devices, and in chemical and food packaging.

Methods for the chemical synthesis of PHCA and PHBA are known. However, chemical synthesis is expensive due to the high energy needed for synthesis and the extensive product purification required. Biological production of these compounds offers a low cost, simplified solution to the problem.

Several methods of producing aromatic carboxylic acids from recombinant microorganisms are described in the literature (see for example commonly owned U.S. Ser. No. 10/439,479; U.S. Pat. No. 6,368,837; and U.S. Pat. No. 6,521,748). However it will be advantageous to optimize production of these molecules for commercial use. One route to optimized production is increased yield. As many of these aromatic carboxylic acids are toxic to the producing host cell, another route may be to minimize the toxic effect the end product has on the host cell. A family of ubiquitous proteins that may be able to address both of these issues are the efflux proteins.

Cellular production of biomolecules can be optimized, in part, by optimizing the expression of efflux transport proteins in the production strain. For example, increased expression of efflux systems for toxic products may be critical for achieving desired rate, titer and yield.

Over 200 transport protein families have been identified, with more than 100 of these transport protein families existing in bacteria (Saier et al., *FASEB J.* 12:265-274 (1998)). At least four superfamilies of drug resistance transporters are known to exist in bacteria. These superfamilies are the ATP Binding Cassette superfamily, the Major Facilitator Superfamily, the Drug/Metabolite Transporter superfamily (Jack et al., *Eur. J. Biochem.* 268:3620-3639 (2001)), and the Resistance-Nodulation-Cell Division family.

Overexpression of an efflux system or its expression from a plasmid vector results in increased resistance of bacteria to a variety of toxic substances, while inactivation of an efflux system causes an increase in sensitivity to antibiotics and toxic substances (Li et al., *J. Bacteriol.* 180:2987-2991 (1998); Ramos, et al., *J. Bacteriol.* 180:3323-3329 (1998)). Such efflux systems are increasingly being recognized in a wide range of bacteria. Comparative amino acid sequence analysis of various transport proteins plus function assays has enabled the identification of a number of distinct families and superfamilies of transport proteins.

U.S. Pat. Nos. 6,225,089 and 6,235,882 issued to Chen (May, 2001) disclose the isolation of a gene encoding a putative efflux protein for solvents and antibiotics. The putative efflux protein, isolated from *Pseudomonas mendocina* ("*P. mendocina*"), is used to examine efflux systems related to solvent tolerance. Culturing *P. mendocina* strains containing altered levels of the gene encoding the putative efflux protein in medium containing increased levels of para-hydroxybenzoic acid results in accumulation of para-hydroxybenzoic acid. The putative efflux protein contains highly conserved regions or motifs that are indicative of proteins in the Major Facilitator Superfamily.

Tolerance of bacteria cells containing efflux pump mutants to para-hydroxybenzoic acid is indicative of the involvement of these efflux pumps in para-hydroxybenzoic acid extrusion (Godoy et al., *J. Bacteriol.* 183:5285-5292 (2001); Ramos-Gonzalez et al., *Appl. Environ. Microbiol.* 67:4338-4341 (2001)). In *Pseudomonas putida* ("*P. putida*"), two efflux pumps, TtgABC and TtgDEF, are speculated to be involved in extrusion of para-hydroxybenzoic acid. Mutation of these efflux pumps, in coordination with increased rigidity of the cell membrane, results in the accumulation of para-hydroxybenzoic acid in *P. putida* strains.

PcaK, a protein also isolated from *P. putida*, is a transporter responsible for the influx of para-hydroxybenzoic acid (Ditty and Harwood, *J. Bacteriol.* 181:5068-5074 (1999)). This transporter, a member of the Major Facilitator Superfamily, also participates in chemotaxis to extracellular para-hydroxybenzoic acid. PcaK does not, however, transport benzoic acid into the cell. Expression of wild-type PcaK protein in *Escherichia coli* ("*E. coli*") results in increased accumulation of para-hydroxybenzoic acid compared to *E. coli* expressing a PcaK mutant.

U.S. Pat. No. 5,292,643 issued to Shibano et al. on Mar. 8, 1994 describes genes related to fusaric acid resistance in a variety of microorganisms. Specifically, genes capable of decomposing or detoxifying fusaric acid are disclosed. One of the genes postulated to be involved in fusaric acid resistance, fusB, shares some homology with the PET yhcP gene (Paulsen et al., *FEMS Microbiol. Lett.* 156:1-8 (1997)).

Applicants incorporate by reference the co-owned and concurrently filed application entitled "Regulator/Promoter for Tunable Gene Expression and Metabolite Sensing", U.S. Patent Application No. 60/440,965.

Recently, the PET family of proteins in bacteria, yeast, and green plants was identified using bioinformatics techniques (Harley and Saier, *J. Mol. Microbiol. Biotechnol.* 2:195-198 (2000)).

The problem to be solved therefore is to enhance the production of aromatic carboxylic acids without compromising the production host due to increased toxicity to the end product. Applicants have solved the stated problem through the discovery that a family of efflux proteins encoded by the yhcRQP operon, both increases the flux of the carboxylic acids from the cell to the medium and lowers toxicity of the cell to the carboxylic acid end product.

SUMMARY OF THE INVENTION

The invention relates to enhancing the production of aromatic carboxylic acids via the up-regulation of a family of efflux proteins encoded by the yhcRQP operon. The elements of the operon may be endogenous to the host cell, or may be introduced via standard recombinant techniques. An additional benefit of the up-regulation of this operon is the increase in resistance the host cell attains to the aromatic carboxylic acid end product.

Accordingly it is an object of the invention to provide a method of increasing the yield of an aromatic carboxylic acid from a host cell producing said aromatic carboxylic acid comprising:

a) providing a host cell which:
   i) produces an aromatic carboxylic acid; and
   ii) comprises all or a subset of the genes comprising the yhcRQP operon; and
b) up-regulating the expression of all or a subset of the genes comprising the yhcRQP operon whereby the yield of aromatic carboxylic acid is increased.

Similarly the invention provides a method for increasing the resistance of a host cell to aromatic carboxylic acids comprising:

a) providing a host cell which comprises all or a subset of the genes comprising the yhcRQP operon; and
b) up-regulating the expression of all or a subset of the genes comprising the yhcRQP operon whereby the host cell resistance to aromatic carboxylic acids is increased.

In a preferred embodiment the host-cell is an enteric bacteria.

Chimeric genes useful for the practice of the methods of the invention are additionally provided comprising an isolated nucleic acid molecule having a nucleic acid sequence selected from the group consisting of SEQ ID NO:1-4; and a promoter; wherein the promoter is heterologous to the isolated nucleic acid molecule.

SEQUENCE DESCRIPTIONS

The invention can be more fully understood from the following detailed description and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the yhcP gene.

SEQ ID NO:2 is the nucleotide sequence of the yhcQ gene.

SEQ ID NO:3 is the nucleotide sequence of the yhcQP operon.

SEQ ID NO:4 is the nucleotide sequence of the yhcRQP operon.

SEQ ID NO:5 is the amino acid sequence of the YhcP protein.

SEQ ID NO:6 is the nucleotide sequence of the primer yhcRQP_left_907.

SEQ ID NO:7 is the nucleotide sequence of the primer yhcRQP_right_907.

SEQ ID NO:8 is the nucleotide sequence of the primer yhcp_left_928.

SEQ ID NO:9 is the nucleotide sequence of the primer yhcQ_right.

SEQ ID NO:10 is the nucleotide sequence of the primer yhcQ-left.

SEQ ID NO:11 is the nucleotide sequence of the primer yhcR_right-928.

SEQ ID NO:12 is the nucleotide sequence of the primer yhcP-Left.

SEQ ID NO:13 is the nucleotide sequence of the primer yhcP-Right.

SEQ ID NO:14 is the nucleotide sequence of the primer Kan-2FP(PCR).

SEQ ID NO:15 is the nucleotide sequence of the primer Kan-2RP(PCR).

SEQ ID NO:16 is the nucleotide sequence of the primer YhcP_TnSense.

SEQ ID NO:17 is the nucleotide sequence of the primer YhcP_TnAntisense.

SEQ ID NO:18 is the nucleotide sequence of the primer Kan-2FP-1.

SEQ ID NO:19 is the nucleotide sequence of the primer Kan-2RP-1.

SEQ ID NO:20 is the nucleotide sequence of the primer YhcS.F.

SEQ ID NO:21 is the nucleotide sequence of the primer YhcS.R.

DETAILED DESCRIPTION OF THE INVENTION

The present invention relates to methods for the enhanced production of various aromatic carboxylic acids including pHBA, pHCA and cinnamic acid (CA). These compounds are generally useful as monomers in liquid crystalline polymers and their bioproduction offers a commercially favorable substitute to existing chemical processes.

Applicants specifically incorporate the entire content of all cited references in this disclosure.

In the context of this disclosure, a number of terms shall be utilized.

The term "pHBA" is the abbreviation for para-hydroxybenzoic acid, which is also known as para-hydroxybenzoate.

The term "pHCA" is the abbreviation for para-hydroxycinnamic acid, which is also known as para-hydroxycinnamate.

The term "CA" is the abbreviation for cinnamic acid, which is also known as cinnamate.

The term "MIC" is the abbreviation for minimum inhibitory concentration.

An "isolated nucleic acid molecule" refers to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor, N.Y. (1989), particularly Chapter 11 and Table 11.1 therein (entirely incorporated herein by reference) (hereinafter "Sambrook"). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS is increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by a second wash in 0.2×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook supra). For hybridizations with shorter nucleic acids, i.e., oligonucleotides, the position of mismatches becomes more important, and the length of the oligonucleotide determines its specificity (Sambrook supra). In one embodiment the length for a hybridizable nucleic acid is at least about 10 nucleotides. Preferably, a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" refers to an amino acid or nucleotide sequence which comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403-410 (1993). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid molecule comprising the primers. Accordingly, a "substantial portion" of a nucleotide sequence comprises enough of the sequence to afford specific identification and/or isolation of a nucleic acid molecule comprising the sequence. The instant specification teaches partial or complete amino acid and nucleotide sequences encoding one or more particular bacterial proteins. The skilled artisan, having the benefit of the sequences as reported herein, may now use all or a substantial portion of the disclosed sequences for the purpose known to those skilled in the art. Accordingly, the instant invention comprises the complete sequences as reported in the accompanying Sequence Listing, as well as substantial portions of those sequences as defined above.

The term "complementary" describes the relationship between nucleotide bases that are capable to hybridizing to one another. For example, with respect to DNA, adenosine is complementary to thymine and cytosine is complementary to guanine. Accordingly, the instant invention also includes isolated nucleic acid molecules that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data*, Part I (Griffin, A. M., and Griffin, H. G., eds.) Humana Press, New Jersey (1994); *Sequence Analysis in Molecular Biology* (von Heinje, G., ed.) Academic Press, New York (1987); and *Sequence Analysis Primer* (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, using the Needleman and Wunsch algorithm with their standard default values of gap creation penalty=12 and gap extension penalty=4 (Devereux et al., *Nucleic Acids Res.* 12:387-395 (1984)), BLASTP, BLASTN, and FASTA (Pearson et al, *Proc. Natl. Acad. Sci. USA* 85:2444-2448 (1988). The BLASTX program is publicly available from NCBI and other sources (BLAST Manual, Altschul et al., Natl. Cent. Biotechnol. Inf., Natl. Library Med. (NCBI NLM) NIH, Bethesda, Md. 20894; Altschul et al., *J. Mol. Biol.* 215:403-410 (1990); Altschul et al., *Nucleic Acids Res.* 25:3389-3402 (1997)). Another preferred method to determine percent identity is by the method of DNASTAR protein alignment protocol using the Jotun-Hein algorithm (Hein et al., *Meth. Enzymol.* 183:626-645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy-terminal positions of the reference amino acid sequence or anywhere between those terminal positions, interspersed either individually among residues in the reference sequence or in one or more contiguous groups within the reference sequence.

The term "percent homology" refers to the extent of amino acid sequence identity between polypeptides. When a first amino acid sequence is identical to a second amino acid sequence, then the first and second amino acid sequences exhibit 100% homology. The homology between any two polypeptides is a direct function of the total number of matching amino acids at a given position in either sequence, e.g., if half of the total number of amino acids in either of the two sequences is the same then the two sequences are said to exhibit 50% homology.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature.

"Genome" refers to the entire genetic information contained within an organism (e.g., chromosome, plasmid, plastid, or mitochondrial DNA). "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. "Structural gene" refers to a gene that codes for the amino acid sequence of a protein or for a ribosomal RNA or transfer RNA. An "operon" refers to a controllable unit of transcription consisting of a number of structural genes transcribed together.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

"Heterologous" as used in the context of gene expression relates to that which is "foreign" to a particular environment. Thus, a "heterologous gene" or "heterologous nucleic acid molecule" means a nucleic acid molecule that is foreign, or non-native to a particular host or genome. Additionally a chimeric gene may comprise heterologous regulatory regions operably linked to a coding nucleic acid, where the promoter may be from an entirely different genome from the coding region, or simply from another part of the same genome, but non-native to the coding region. A "heterologous protein" is a protein that is foreign to a host cell and is typically encoded by a heterologous gene.

"Host cell" refers to a cell into which has been introduced (e.g., transformed or transfected) an exogenous polynucleotide sequence, i.e. a heterologogus nucleic acid molecule. Host cells are typically prokaryotic cells such as bacteria, e.g., *E. coli*, and may be eukaryotic cells such as yeast, insect, amphibian, green plant, or mammalian cells, where the relevant regulator genes exist.

"Translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner et al., *Mol. Biotechnol.* 3:225 (1995)).

"3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet and has an effect on cellular processes.

The term "operably linked" refers to the association of nucleic acid sequences on a single nucleic acid molecule so that the function of one is affected by the other. For example, a promoter is operably linked with a coding sequence when it affects the expression of that coding sequence (i.e., that the coding sequence is under the transcriptional control of the promoter). Coding sequences can be operably linked to regulatory sequences in sense or antisense orientation.

The term "expression" refers to the transcription and stable accumulation of sense (mRNA) or antisense RNA derived from the nucleic acid molecule of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or nontransformed organisms. "Co-suppression" refers to the production of sense RNA transcripts capable of suppressing the expression of identical or substantially similar foreign or endogenous genes (U.S. Pat. No. 5,231,020).

"Transformation" refers to the transfer of a nucleic acid molecule into the genome of a host organism, resulting in genetically stable inheritance. Host organisms containing the transformed nucleic acid fragments are referred to as "transgenic" organisms.

The terms "plasmid", "vector" and "cassette" refer to an extra chromosomal element often carrying genes that are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

"PCR" or "polymerase chain reaction" is a technique used for the amplification of specific DNA segments (U.S. Pat. Nos. 4,683,195 and 4,800,159).

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Sambrook"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention relates to the discovery that a family of efflux proteins encoded by the yhcRQP has the ability to enhance the production of aromatic carboxylic acids from host cells producing the same. Additionally it has been found that host cells where these efflux proteins are up-regulated, possess increased tolerance to toxicity by the carboxylic acid end product.

The YhcP Efflux Pump

The YhcP pump is in phylogenetic family for which no members have previously been demonstrated to function as efflux pumps. The predicted membrane topology of this family of proteins is different from other characterized transport proteins. In plants these proteins have six predicted N-terminal transmembrane domains and a large C-terminal cytoplasmic domain. In yeast and gram negative bacteria, these proteins have 12 predicted transmembrane domains that are organized as two repeated units of six transmembrane domains with a large cytoplasmic domain. Thus, YhcP represents a novel efflux mechanism.

Applicants observed that expression of the yhcP gene (along with two other co-transcribed genes yhcQ and yhcR) is highly upregulated upon treatment of *E. coli* cells with aromatic carboxylic acids, such a pHBA, pHCA, and CA, and, as a result of this observation, it was speculated that such molecules might be substrates for the YhcP efflux pump. This was demonstrated by showing that a yhcP null mutant of *E. coli* was hypersensitive to pHBA and to pHCA. Furthermore, expression of the yhcRQP operon from a non-native promoter on a multicopy plasmid confers increased resistance to pHCA, thus demonstrating that manipulation of this efflux system can increase the tolerance of *E. coli*. Informatics analysis identified a class of putative efflux transport proteins in bacteria, yeast, and plants (Harley, K T and Saier, M H, *J. Mol. Microbiol Biotechnol.* 2:195-198 (2000)). However, to Applicants' knowledge, no experimental evidence of this function has been published, nor have any predictions for substrates been made.

Generally, it is known that cellular production of biomolecules can be optimized, in part, by optimizing the expression of efflux transport proteins in the production host. Multicopy expression of the *E. coli* yhcRQP operon yields increased resistance to exogenously added pHCA. Presumably, similar manipulation of this efflux system in a host expressing genes for pHCA biosynthesis would likewise result in increased tolerance to pHCA produced intracellularly. Thus, this and related efflux transport systems may be used to increase the tolerance of the production organism to toxic products, thereby improving rate, titer and yield. Maximizing the amount of extracellular product can also elevate the recovered yield of biomolecules, because often product contained in the cell biomass is not recovered. Additionally, elevated efflux of molecules that are inhibitors or repressors of expression of enzymes involved in their biosynthesis will allow higher levels of production. On the other hand, decreasing efflux of compounds that are intermediates in a bioprocess can improve the efficiency of a metabolic pathway. Thus, manipulation of host cells by increasing or decreasing levels of PET proteins can be used to maximize extracellular production of desired biomolecules. Proteins related to YhcP of *E. coli*, the PET family, have been found in bacteria, yeast, and green plants. Thus, members of this family of efflux proteins may be useful for engineering both prokaryotic and eukaryotic systems for optimized small molecule production.

*E. coli* YhcP efflux pump has a relatively narrow range of substrate specificity. This specificity is in contrast to several multidrug efflux pumps that efflux a broad range molecules. The advantage of a more specific efflux pump is that it allows targeting of a small set of molecules for export outside of the cell. Other members of the PET family are likely to have differing substrate specificity and, thus, export of other classes of molecules may be possible with other members of this protein family. Furthermore, mutagenesis, gene shuffling, or other methods that result in modified proteins can potentially be applied to alter the substrate range of this efflux pumps in this family.

This family of efflux proteins may be useful for engineering both prokaryotic and eukaryotic systems for optimized small molecule production in bioengineered host strains. The expression of these efflux pumps can be increased by forming chimeric genetic constructs in the host strain that place the efflux pump genes under control of strong promoter sequences. Expression levels can also be increased by increasing the copy number of the efflux genes, such as by cloning into a multicopy plasmid with subsequent transformation of the host strain. The resultant increased levels of efflux protein would result in increased efflux of the cognate small molecule substrates, which would be expected to improve the tolerance of the production host to the small molecule, increase the extracellular yield of the small molecule, and reduce enzyme inhibition by the small molecule. Conversely, lowering the expression of the appropriate efflux pumps would be desirable if it is advantageous to keep a small molecule within the production host cell, such as if the molecule is an intermediate in an metabolic pathway to the desired product molecule. This can be accomplished by mutation of the gene encoding the efflux pump.

Placement of appropriate efflux genes under the control of strong promoters or on multicopy plasmids, or both, in a production strain that has been engineered to produce aromatic carboxylic acids will result in increased extracellular concentrations of the aromatic carboxylic acid, thereby increasing the yield.

Removing a toxin from a host cell can be accomplished by increasing the expression levels of efflux pumps that pump the toxic molecule out of the cell. Placement of appropriate efflux genes under the control of strong promoters or on multicopy plasmids, or both, in a host cell that produces a toxin or is exposed to the toxin extracellularly will result in more rapid removal of the toxin from the host cell. This increased removal rate of the toxin would improve the tolerance of the host cell to the toxin.

Endogenous yhcRQP Operons

Those cells having existing homologous yhcRQP operons may be used in the present invention in hosts producing aromatic carboxylic acids. A number of such operons has been identified in the literature. For example the yhcRQR operon is known in a variety of enteric bacteria such as *Escherichia* (Hayashi et al., "Complete genome sequence of enterohemorrhagic *Escherichia coli O*157:H7 and genomic comparison with a laboratory strain K-12", *DNA Res.* 8 (1), 11-22 (2001)); *Yersinia* (Parkhill et al., "Genome sequence of *Yersinia pestis*, the causative agent of plague", *Nature* 413 (6855), 523-527 (2001)); *Shigella* (Wei et al., "Complete Genome Sequence and Comparative Genomics of *Shigella flexneri* Serotype 2a Strain 2457T", *Infect. Immun.* 71 (5), 2775-2786 (2003)); and *Salmonella* (McClelland et al., "Complete genome sequence of *Salmonella enterica serovar* Typhimurium LT2"; *Nature* 413 (6858), 852-856 (2001)). It will be appreciated by one of skill in the art that those organisms having homologs to the present operon will be expected to function in the method of the invention. Thus a *Salmonella* or *Shigella* strain, as described above, may be used in this fashion. Host cells suitable for use in the present invention will include but are not limited to *Escherichia, Salmonella, Bacillus, Acinetobacter, Streptomyces, Methylobacter, Rhodococcus, Corynebacterium, Pseudomonas, Rhodobacter*, and *Synechocystis.*

Particularly suitable in the present invention are members of the enteric class of bacteria. Enteric bacteria are members of the family Enterobacteriaceae and include such members as *Escherichia, Salmonella*, and *Shigella*. They are gram-negative straight rods, 0.3-1.0×1.0-6.0 mm, motile by *peritrichous flagella* (except for *Tatumella*) or nonmotile. They grow in the presence and absence of oxygen and grow well on peptone, meat extract, and (usually) MacConkey's media. Some grow on D-glucose as the sole source of carbon, whereas others require vitamins and/or mineral(s). They are chemoorganotrophic with respiratory and fermentative metabolism but are not halophilic. Acid and often visible gas is produced during fermentation of D-glucose, other carbohydrates, and polyhydroxyl alcohols. They are oxidase negative and, with the exception of *Shigella dysenteriae* 0 group 1 and *Xenorhabdus nematophilus*, catalase positive. Nitrate is reduced to nitrite (except by some strains of *Erwinia* and *Yersina*). The G+C content of DNA is 38-60 mol % ($T_m$, Bd). DNAs from species within most genera are at least 20% related to one another and to *Escherichia coli*, the type species of the family. Notable exceptions are species of *Yersina, Proteus, Providenica, Hafnia* and *Edwardsiella*, whose DNAs are 10-20% related to those of species from other genera. Except for *Erwinia chrysanthemi*, all species tested contain the enterobacterial common antigen (Bergy's Manual of Systematic Bacteriology, D. H. Bergy et al., Baltimore: Williams and Wilkins, 1984).

Isolation of yhcRQP Homologs

It is clear that host cells comprising the present homologs of the yhcRQP operon are suitable for use in the invention. However, where it is desired to find new strains having the present operon, or to identify new efflux encoding genes having greater functionality in non-native host cells, it will be possible to use the sequence information provided in the literature and in this disclosure to identify and isolate such homologs.

A specific yhcRQP operon has been identified and isolated from *E. coli*. SEQ ID NO:1 sets forth the nucleic acid sequence of the yhcP gene; SEQ ID NO:2 sets forth the nucleic acid sequence of the yhcQ gene; SEQ ID NO:3 sets forth the nucleic acid sequence of the yhcQP gene combination and SEQ ID NO:4 sets forth the nucleic acid sequence of the entire yhcRQP operon.

It will be apparent to the skilled artisan that homologs to the *E. coli* sequences or others cited in the literature may easily be identified based on current practices in molecular biology, and such homologs will be equally applicable and useful in the present invention. For example, one of skill in the art may use the nucleic acid molecules of the instant invention to isolate cDNAs and genes encoding homologous PET (putative efflux transporter) proteins from the same or other bacterium species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., PCR or ligase chain reaction).

For example, PET genes, either as cDNAs or genomic DNAs, could be isolated directly by using all or a portion of the instant nucleic acid molecules as DNA hybridization probes to screen libraries from any desired bacterium employing methodology well known to those skilled in the art. Specific oligonucleotide probes based upon the instant PET gene sequence can be designed and synthesized by methods known in the art (Sambrook, Supra). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid molecules may be used in polymerase chain reaction protocols to amplify longer nucleic acid molecules encoding homologous PET genes from DNA or RNA. The polymerase chain reaction may also be performed on a library of cloned nucleic acid molecules wherein the sequence of one primer is derived from the instant nucleic acid molecules, and the sequence of the other primer takes advantage of the presence of the polyadenylic acid tracts to the 3' end of the mRNA precursor. Alternatively, the second primer sequence may be based upon sequences derived from the cloning vector. For example, the skilled artisan can follow the RACE protocol (Frohman et al., *Proc. Natl. Acad. Sci. USA* 85:8998-9002 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Invitrogen, Carlsbad, Calif.), specific 3' or 5' cDNA fragments can be isolated (Ohara et al., *Proc. Natl. Acad. Sci. USA* 86:5673-5677 (1989); Loh et al., *Science* 243:217-220 (1989)). Products generated by the 3' and 5' RACE procedures can be combined to generate full-length cDNAs (Frohman et al., *Techniques* 1:165 (1989)).

Alternatively the yhcRQP sequences may be employed as an hybridization reagent for the identification of homologs. The basic components of a nucleic acid hybridization test include a probe, a sample suspected of containing the gene or gene fragment of interest, and a specific hybridization method. Probes are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151(1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1M sodium chloride, about 0.05 to 0.1M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kilodaltons), polyvinylpyrrolidone (about 250-500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Enhanced Production of Aromatic Carboxylic Acids

Once a host cell comprising a yhcRQP operon has been identified or constructed it will be necessary to engineer its up-regulation. This may be accomplished by placing the relevant genes on a multicopy plasmid and transfecting the cell. Alternatively, where the operon is resident in the genome of the host cell, up-regulation may be effected by inserting a strong promoter upstream of the operon, such as promoter from the following genes lac, trp, $IP_L$, $IP_R$, T7, tac, and trc.

A variety of cells produce aromatic carboxylic acids naturally. Many of these are green plants such as soybean, rapeseed (*Brassica napus, B. campestris*), sunflower (*Helianthus annus*), Jerusalem artichoke (*Helianthus tuberosis*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa*, L), sorghum (*Sorghum bicolor*), rice (*Oryza sativa*), Arabidopsis, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

Other cells may have to be engineered to produce aromatic carboxylic acids. A variety of methods for such engineering have been disclosed (see for example U.S. Pat. No. 6,368,837; and U.S. Pat. No. 6,521,748, incorporated herein by reference). Aromatic carboxylic acids particularly suitable in the present invention include but are not limited to para-hydroxybenzoic acid, para-hydroxycinnamic acid, cinnamic acid, salicylic acid, benzoic acid, and 1-napthoic acid.

EXAMPLES

The present invention is further defined in the following Examples, in which all parts and percentages are by weight and degrees in Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

General Methods

Standard recombinant DNA and molecular cloning techniques used in the Examples are well known in the art and are described by Sambrook, J., Fritsch, E. F. and Maniatis, T., *Molecular Cloning: A Laboratory Manual*; Cold Spring Harbor Laboratory Press: Cold Spring Harbor, N.Y. (1989); by T. J. Silhavy, M. L. Bennan, and L. W. Enquist, *Experiments with Gene Fusions*, Cold Spring Harbor Laboratory, Cold Spring Harbor, N.Y. (1984); and by Ausubel, F. M. et al., *Current Protocols in Molecular Biology*, pub. by Greene Publishing Assoc. and Wiley-Interscience, Hoboken, N.J. (1987).

Standard genetic methods for transduction used in the Examples are well known in the art and are described by Miller, J. H., *Experiments in Molecular Genetics*, Cold Spring Harbor Laboratory Press, Cold Spring Harbor, N.Y. (1972).

The meaning of abbreviations is as follows: "kb" means kilobase(s), "bp" means base pairs, "hr" means hour(s), "min" means minute(s), "sec" means second(s), "d" means day(s), "l" means liter(s), "ml" means milliliter(s), "μl" means microliter(s), "nl" means nanoliter(s), "μg" means microgram(s), "ng" means nanogram(s), "mM" means millimolar, "μM" means micromolar, "nm" means nanometer(s), "μmol" means micromole(s), "RLU" means relative light units, and "CFU" means colony forming unit(s).

Media and Culture Conditions:

Materials and methods suitable for the maintenance and growth of bacterial cultures were found in *Experiments in Molecular Genetics* (Jeffrey H. Miller), Cold Spring Harbor Laboratory Press, Cold Spring Harbor, N.Y. (1972); *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds), pp. 210-213, American Society for Microbiology, Washington, D.C. (1981); or Thomas D. Brock in *Biotechnology: A Textbook of Industrial Microbiology*, Second Edition (1989) Sinauer Associates, Inc., Sunderland, Mass. All reagents and materials used for the growth and maintenance of bacterial cells were obtained from Aldrich Chemicals (Milwaukee, Wis.), BD Diagnostic Systems (Sparks, Md.), Invitrogen Corp. (Carlsbad, Calif.), or Sigma Chemical Company (St. Louis, Mo.) unless otherwise specified.

LB medium contains the following per liter of medium: Bacto-tryptone (10 g), Bacto-yeast extract (5 g), and NaCl (10 g).

Vogel-Bonner medium contains the following per liter: 0.2 g $MgSO_4.7H_2O$, 2 g citric acid.$1H_2O$, 10 g $K_2HPO_4$ and 3.5 g $NaNH_4HPO_4.4H_2O$.

Minimal M9 medium contains the following per liter of medium: $Na_2HPO_4$ (6 g), $KH_2PO_4$ (3 g), NaCl (0.5 g), and $NH_4Cl$ (1 g).

Above media were autoclaved for sterilization then 10 ml of 0.01 M $CaCl_2$ and 1 ml of 1 M $MgSO_4.7H_2O$ were added to M9 medium. Vitamin B1 (thiamin) was added at 0.0001% to both Vogel-Bonner and M9 media. Carbon source and other nutrients and supplements were added as mentioned in the Examples. All additions were pre-sterilized before they were added to the media.

Molecular Biology Techniques:

Restriction enzyme digestions, ligations, transformations, and methods for agarose gel electrophoresis were performed as described in Sambrook, Supra. Polymerase Chain Reactions (PCR) techniques were found in White, B., *PCR*

*Protocols: Current Methods and Applications*, Volume 15 (1993) Humana Press Inc, Totowa, N.J.

Example 1

Evidence of Efflux Function of a Putative Efflux Transporter

An *E. coli* library of transposon insertion mutations was constructed using the transposome system based on the Tn5 transposon (Epicentre, Madison, Wis.). A transposome is a protein-DNA complex composed of the EZ::TN<Kan-1> transposon and the EZ::TN transposase. The EZ::TN transposase is bound to the ends of the transposon, which facilitates the formation of a stable synaptic complex. The transposome requires $Mg^{+2}$ to initiate the insertion of the EZ::TN<Kan-1> transposon into target DNA. The cellular levels of $Mg^{+2}$ are sufficient to activate the transposome. Thus, the electroporation of the transposome into cells permits the in vivo insertion of the EZ::TN<Kan-1> transposon into bacterial genomes.

The EZ::TN<Kan-1> transposome was electroporated into electroporation competent *E. coli* strain DH5αE cells (Invitrogen, Carlsbad, Calif.). Following electroporation, the cells were grown in SOC medium (Invitrogen) for one hour at 37° C. with aeration. Subsequently, the cells were plated onto LB agar plates containing kanamycin (50 μg/ml) (LB+Kan) and incubated overnight at 37° C. Individual colonies were inoculated into 96-well microtiter plates containing 150 μl of LB+Kan and incubated overnight at 37° C.

"Single Primer PCR" was used to determine the identity of each *E. coli* transposon mutation. Using a single DNA primer that was complementary to one end of the EZ::TN<Kan-1> transposon, PCR products were generated. Subsequently, a second DNA primer (located internal and adjacent to the PCR primer) was used to sequence the PCR products. The DNA primer used in the PCR reaction was either Kan-2FP(PCR) (SEQ ID NO:14) or Kan-2RP(PCR) (SEQ ID NO:15), and the DNA primer used for DNA sequencing was either Kan-2FP(PCR) (SEQ ID NO:14) or Kan-2RP(PCR) (SEQ ID NO:15), respectively. The PCR reaction conditions were the following: (1) 94° C., 15 minutes (2) 20 cycles—94° C., 30 seconds; 60° C., 30 seconds; 72° C., 3 minutes (3) 30 cycles—94° C., 30 seconds; 40° C., 30 seconds; 72° C., 2 minutes (4) 30 cycles—94° C., 30 seconds; 60° C., 30 seconds; 72° C., 2 minutes (5) 72° C., 7 minutes. The PCR reactions were prepared for DNA sequencing using the QIAquick PCR Purification Kit (Qiagen, Valencia, Calif.).

One TN<Kan> insertion in the *E. coli* chromosome was at nucleotide 3,385,409 with respect to the *E. coli* genomic sequence. Accordingly, this insertion is 1553 nucleotides from the 3' end of the yhcP gene, which is 1968 nucleotides in length. The location of this insertion was confirmed using PCR amplification with primers YhcP_TnSense (SEQ ID NO:16) and YhcP_TnAntisense (SEQ ID NO:17). The product of the PCR reaction with template from strains with the yhcP::TN<Kan> mutation was approximately 1.6 kb. In control PCR reactions, using template from $yhcP^+$ strains, the PCR product was approximately 0.3 kb.

The sensitivity of this mutant *E. coli* strain, DPD2443, to para-hydroxybenzoic acid (pHBA) was compared with that of the otherwise isogenic parental strain DH5αE. A zone of growth inhibition test was done using 0.1 ml of overnight cultures in LB medium plated onto LB agar plates using 2.5 ml LB soft agar. The zone of growth inhibition surrounding a disk containing 90 μmol of the pHBA sodium salt (Sigma Chemical Company) was measured after 24 hr incubation at 37° C. The results shown in Table 1 demonstrate hypersensitivity of the yhcP mutant strain to pHBA.

TABLE 1

Sensitivity of *E. coli* strains to pHBA

| *E. coli* strain name | Genotype | pHBA zone of growth inhibition, mm diameter (relative clarity) |
|---|---|---|
| DH5αE | Parental | 9.0 (turbid) |
| DPD2443 | yhcP::TN<Kan> of DH5αE | 13.0 (very slightly turbid) |

The yhcP::TN<Kan> was introduced into *E. coli* strain MG1655 (obtained from Prof. Douglas Berg, Washington University School of Medicine, St. Louis, Mich.) by P1clr100 Cm mediated transduction to kanamycin resistance using phage lysates of *E. coli* strain DPD2443. One of the resultant kanamycin resistant transductants was named DPD2444. This strain was compared with the otherwise isogenic parental strain, MG1655, for sensitivity to pHBA and to pHCA. For this test, the MIC (minimum inhibitory concentration) was determined as the lowest concentration from a series of 2-fold dilutions that resulted in complete growth inhibition after overnight growth of a 100 μl culture at 37° C. in Vogel-Bonner defined medium with 0.4% glucose as the carbon source. The results in Table 2 demonstrate hypersensitivity of the yhcP mutant strain to pHBA and pHCA.

TABLE 2

Sensitivity of *E. coli* strains to pHCA and pHBA

| *E. coli* strain name | Genotype | MIC for pHCA, mM | MIC for pHBA, mM |
|---|---|---|---|
| MG1655 | + | 50 | 200 |
| DPD2444 | yhcP::TN<Kan> | 12 | 25 |

The results from this Example, when interpreted in the light of the efflux function predicted by informatic analysis, provide convincing evidence that yhcP gene encodes an efflux pump for which pHBA and pHCA are substrates. Accordingly, the absence of this efflux pump results in increased intracellular concentrations of pHBA or pHCA, which in turn is manifested as the hypersensitive phenotype.

Example 2

Manipulation of the Efflux Transporter and Neighboring Genes to Confer Hyper-Resistance to pHCA The *E. coli* yhcP gene is predicted to be cotranscribed with two nearby genes that have the same direction of transcription, yhcQ and yhcR. The order of genes in this putative operon is yhcRQP. The product of yhcQ has been predicted to function in cellular efflux because it is a member of the "membrane fusion protein" family, for which several other members are known to function in efflux systems. Furthermore, the product of yhcQ has been predicted to have an alpha-helical barrel similar to that found in the TolC protein, a channel used for efflux of molecules across the outermembrane of gram negative bacteria; however, the significance of the predicted structure is not known. The third gene of the predicted operon, yhcR, encodes a protein for which no prediction of function has been made.

Plasmid pDEW668 contained the *E. Coli* yhcRQP operon under control of the trc promoter in a multicopy plasmid. To construct this plasmid, the yhcRQP operon was obtained by PCR amplification using chromosomal DNA from *E. coli* strain MG1655 as template and the primers yhcRQP_left__907 (SEQ ID NO:6) and yhcRQP_right__907 (SEQ ID NO:7).

The yhcRQP_right__907 primer was designed so that when the amplified DNA was cloned into pTrcHis2 TOPO® vector, an N-terminal fusion protein would not be formed and thus the native YhcR protein was expressed. The yhcRQP_right__907 primer also had an EcoRI site that was used to determine orientation of the inserted DNA. The yhcRQP_left__907 primer was designed to contain the termination codon of yhcP and thus expressed the native YhcP protein, rather than a fusion protein.

A 3217 bp PCR product was obtained from amplification reactions using ExTaq™ (TaKaRa, Madison, Wis.) and the following conditions: 94° C. for 5 minutes, 35 cycles of (94° C. for 1 minute, 60° C. for 2 minutes, 72° C. for 3 minutes), and 72° C. for 15 minutes. The product of the PCR reaction was purified using a Qiaquick PCR clean-up kit (Qiagen) following the manufacturers instructions and was then ligated into pTrcHis2TOPO® (Invitrogen) following the protocol supplied by the vendor. After transformation of *E. coli* strain TOP10 (Invitrogen) and selection for Ampicillin resistance, plasmid DNA from individual transformants was digested with EcoRI. One plasmid, for which two fragments of sizes 4.4 kb (vector) and 3.2 kb (insert) resulted, was named pDEW668. The presence of the yhcRQP operon in the correct orientation was confirmed by DNA sequence analysis of the ends of the insert DNA in pDEW668. Plasmid pDEW668 and a control plasmid, pTrcHis2TOPO®/lacZ (Invitrogen), were moved by transformation to *E. coli* strain MG1655, selecting for Ampicillin resistance, to generate strains DPD3314 and DPD3313, respectively.

The pHCA MICs for *E. coli* strains DPD3313 and DPD3314 were determined. The MIC was defined as the lowest concentration of a series of 2-fold dilutions that resulted in complete growth inhibition after overnight growth of a 100 μl culture at 37° C. in Vogel-Bonner defined medium with 0.4% glucose as the carbon source. IPTG was not added to the medium because the trc promoter has substantial activity in its absence. The results in Table 3 show that multicopy expression of the yhcRQP operon resulted in two-fold increased resistance of a non-mutant *E. coli* strain, MG1655, to pHCA. This result demonstrates that increased tolerance to pHCA can be achieved through manipulation of this novel efflux transporter.

TABLE 3 pHCA MICs for *E. coli* strains

| *E. coli* strain name | Plasmid | Host | MIC for pHCA, mM |
|---|---|---|---|
| DPD3313 | pTrcHis2TOPO ®/lacZ (lacZ gene expressed from the trc promoter) | MG1655 | 50 |
| DPD3314 | pDEW668 (multicopy yhcRQP in pTrcHis2TOPO ®) | MG1655 | 100 |

Example 3

Hypersensitive *E. coli* Strains Lacking a Regulator of yhcRQP Expression

The yhcS gene of *E. coli* encodes an uncharacterized member of the LysR family of positive acting regulatory molecules. This gene is located immediately adjacent to the yhcRQP operon in the *E. coli* genome. The possibility that YhcS controls expression of yhcRQP was tested using a yhcS null mutation. This mutation was found in the library of mutations described in Example 1. The yhcS transposon mutant was identified using PCR amplification primer Kan-2FP(PCR) (SEQ ID NO:14) and DNA sequencing primer Kan-2FP-1 (SEQ ID NO:18). The transposon mutation was confirmed using gene-specific primers: YhcS.F (SEQ ID NO:20) and YhcS.R (SEQ ID NO:21) and transposon-specific primers Kan-2FP-1 (SEQ ID NO:18) and Kan-2RP-1 (SEQ ID NO:19).

The size of the yhcS gene is ~929 base pairs. The transposon insertion site within the yhcS gene is ~330 base pairs away from the 5' end of yhcS. A PCR reaction done with the YhcS.F and Kan-2RP-1 primers yielded a PCR fragment ~550 base pairs and PCR primers YhcS.R and Kan-2FP-1 yielded a PCR product <400 base pairs in size.

*E. coli* strain DPD2410 is DH5αE containing the yhcS::TN<Kan> mutation. A derivative of *E. coli* strain MG1655 with the yhcS::TN<Kan> mutation was made by P1clr100 Cm mediated transduction using phage grown on strain DPD2410 as a donor and selection for kanamycin resistance. The presence of the yhcS::TN<Kan> mutation in one of the resultant transductants, named DPD2433, was confirmed by PCR amplification.

Plasmid pDEW655 was constructed by ligating an *E. coli* chromosomal segment between nucleotides 3385829 and 3386761 according to the *E. coli* genomic sequence, which contains the promoter region of the putative yhcRQP operon and the entire yhcR gene and the 5' end of the yhcQ gene, to the luxCDABE genes parental plasmid, pDEW201 (Gonye et al. U.S. Patent Application Publication 20030219736). Thus, this gene fusion will report on expression of the yhcQ gene and accordingly any other genes cotranscribed with it. Plasmid pDEW655 was moved to *E. coli* strains MG1655 and DPD2433 by transformation, selecting for Ampicillin resistance to generate strains DPD2436 and DPD2437, respectively. The bioluminescent response of these two strains to pHBA was tested. Aliquots (50 μl) of actively growing cultures at 37° C. in LB medium that had been previously diluted and from overnight cultures in LB medium with 150 μg/ml Ampicillin were added to 50 μl of LB medium at pH 7.0 containing pHBA as the sodium salt form. Several concentrations of pHBA were tested. Table 4 shows the response in these two host strains at thirty minutes after cells were added to pHBA containing medium. The yhcS::TN<Kan> mutation almost completely eliminated the upregulation of expression induced by pHBA treatment at all concentrations tested.

TABLE 4

Bioluminescence response of strains containing the yhcRQP-luxCDABE gene fusion

| | RLU | | Ratio treated/control | |
|---|---|---|---|---|
| [pHBA] | yhcS+ | yhcS− | yhcS+ | ychS− |
| 100 | 0.437 | 0.045 | 0.693 | 0.055 |
| 50 | 91.7 | 0.614 | 145 | 0.753 |
| 25 | 66.6 | 1.59 | 106 | 1.95 |
| 12.5 | 30.8 | 1.82 | 48.8 | 2.23 |
| 6.2 | 16.2 | 1.42 | 25.7 | 1.75 |
| 3.1 | 10.2 | 1.16 | 16.2 | 1.42 |
| 1.6 | 6.72 | 1.02 | 10.6 | 1.25 |
| 0 | 0.631 | 0.815 | 1 | 1 |

The nearly complete lack of induction of yhcRQP expression in the yhcS mutant suggests that cells lacking this regulator may be less effective at efflux of pHBA. This was tested by measuring the size of the zone of growth inhibition and scoring the degree of growth within the zones resulting from the sodium salt of pHBA (80 μmoles/disk) on solidified Vogel-Bonner medium with glucose as the carbon source (Table 5).

TABLE 5 pHBA zone of growth inhibition, average of two experiments

| Strain name | Chromosomal mutation | pHBA zone of growth inhibition, mm diameter |
|---|---|---|
| MG1655 | + | 9.5 turbid |
| DPD2433 | yhcS$^-$ | 20.2 clear |

The strain containing the yhcS mutation was hypersensitive to pHBA.

Example 4

Substrate Specificity of the YhcP Efflux Transporter

Example 1 demonstrated that a strain containing a loss-of-function mutation in the yhcP gene was hypersensitive to pHBA and pHCA. This result provided strong evidence that yhcP encodes an efflux pump for which these two molecules are substrates. To further define substrates of this efflux system, other molecules were tested with this genetic test. That is, likely substrates of the yhcP efflux pump are those compounds for which the yhcP mutant strain is hypersensitive as compared with an otherwise isogenic control strain. *E. coli* strains DPD2444 (yhcP$^-$) and MG1655 (yhcP$^+$) were tested for inhibition by a large number of chemicals at Biolog Inc. (Hayward, Calif.) using the Phenotype MicroArray™ 1-20. The basis of this technology has been described in a recent publication (Bochner et al., *Genome Res.,* 11:1246-1255 (2001)). The chemical sensitivity test was done with 240 compounds at 4 concentrations each. These chemicals included aromatic and heterocyclic molecules, such as acriflavin, dichloro-8-hydroxyquinoline, 9-aminoacridine, fusaric acid, salicylic acid, phenylethanol, o-cresol, m-cresol, p-cresol, pentachlorophenol, coumarin, DL 3-phenyl lactic acid, and cinnamic acid. Also included were numerous antibiotics and other antimicrobial compounds, including several weak acids and other compounds that would disrupt proton flux. Cinnamic acid was the only compound of the 240 tested for which strain DPD2444 was hypersensitive as compared with MG1655. The report regarding the increased sensitivities of strain DPD2444 (strain 16) compared with MG1655 (strain 14) is quoted below in Table 6.

TABLE 6

Phenotype MicroArray ™ results

| | | Name | Strain Number | |
|---|---|---|---|---|
| | Test | *E. coli* | Strain 16 | |
| | Ref | *E. coli* | Strain 14 | |
| Phenotypes Lost - Slower Growth/ Sensitivity | | | | |
| PM | Wells | Test | Difference | Mode of Action |
| PM19 | C 11 | Cinnamic acid | −83 | antimicrobial, from plants |

The score of −83 for cinnamic acid is consistent with a slight, but reproducible difference in growth inhibition between the two strains. The lack of difference between these two strains for each of the other 239 compounds tested suggests that the YhcP efflux pump has a high degree of specificity for certain aromatic carboxylic acids.

Additional compounds were tested for growth inhibition of *E. coli* MG1655 (yhcP$^+$) and DPD2444 (yhcP$^-$) in Vogel-Bonner medium with glucose as the carbon source and with 0.01% tetrazolium violet added as an indicator of viability. A series of two-fold dilutions of each chemical was made to the wells of a clear 96-well microplate in 50 μl volume. To these wells was added 50 μl of an overnight culture in Vogel Bonner medium with glucose as a carbon source of either MG1655 or DPD2444 that had been previously diluted 500-fold into fresh medium. The plates were incubated at 37° C. without shaking for 16 to 18 hours. The purple color in each well was visually scored. A score of 4+ indicated full purple color equivalent to a no chemical control well. Scores of 3+, 2+, or 1+ indicated decreasing amounts of purple color. A score of − indicated the complete absence of color. The MIC was defined as the lowest tested concentration that gave complete absence of color. The rank of difference between strains was defined as the score of pigment color for *E. coli* MG1655 in wells containing the concentration of a given chemical at the MIC for DPD24444. When MG1655 had no color, the score was 0. When MG 1655 was scored at 1+, the score was 1, when scored at 2+, the score was 2, etc. Table 7 summarizes data for compounds tested with these conditions.

TABLE 7

Chemical sensitivities of *E. coli* strains with and without the YhcP efflux pump

| Chemical | MG1655 (yhcP+) | DPD2444 (yhcP−) | Fold Diff | Rank Diff |
|---|---|---|---|---|
| pHBA | 100 mM | 12.5 mM | 8 | 4 |
| 6-hydroxy-2-naphthoic acid | 20 mM | 2.5 mM | 8 | 3 |
| pHCA | 40 mM | 10 mM | 4 | 2 |
| 2-hydroxycinnamate | 20 mM | 10 mM | 2 | 2 |
| 1,5-dihydroxynaphthalene | 0.5 mM | 0.25 mM | 2 | 1 |
| 1,6-dihydroxynaphthalene | 0.5 mM | 0.25 mM | 2 | 1 |
| 2,7-dihydroxynaphthalene | 0.62 mM | 0.31 mM | 2 | 1 |
| 2-naphthoic acid | 20 mM | 10 mM | 2 | 1 |
| CA | 20 mM | 10 mM | 2 | 1 |

TABLE 7-continued

Chemical sensitivities of *E. coli* strains with and without the YhcP efflux pump

| Chemical | MG1655 (yhcP+) | DPD2444 (yhcP−) | Fold Diff | Rank Diff |
|---|---|---|---|---|
| 1,4-naphthalenedicarboxyylic acid | 10 mM | 10 mM | 1 | 0 |
| 1-hydroxy-2-naphthoic acid | 0.62 mM | 0.62 mM | 1 | 0 |
| 1-naphthoic acid | 2.5 mM | 2.5 mM | 1 | 0 |
| 2,3-dihydroxybenzoic acid | 10 mM | 10 mM | 1 | 0 |
| 2,3-naphthalenedicarboxylic acid | 80 mM | 80 mM | 1 | 0 |
| 2,6-dimethoxyphenol | 5 mM | 5 mM | 1 | 0 |
| 3,4-dihydroxycinnamate | 0.62 mM | 0.62 mM | 1 | 0 |
| 3,5-dimethoxy-4-hydroxycinnamate | 10 mM | 10 mM | 1 | 0 |
| 3-hydroxy-2-naphthoic acid | 1.2 mM | 1.2 mM | 1 | 0 |
| Benzoate | 25 mM | 25 mM | 1 | 0 |
| 2-biphenylcarboxylic acid | 2.5 mM | 2.5 mM | 1 | 0 |
| dimethyl sulfoxide (DMSO) | 20% | 20% | 1 | 0 |
| Methyl paraben | 3.8 mM | 3.8 mM | 1 | 0 |
| Salicylate | 100 mM | 100 mM | 1 | 0 |
| Tulipalin | 0.008% | 0.008% | 1 | 0 |

In this test, reliable differences between the two strains are those for which there was both a difference in the MIC between the two strains of at least 2-fold and a rank at least 2. Note that a slight difference in growth inhibition of the two strains by cinnamic acid was observed in this test, but that the degree of distinction was far less than that obtained by pHBA or pHCA treatment. Accordingly, compounds defined as substrates of the YhcP efflux pump by this genetic test are pHBA, pHCA, 6-hydroxy-2-napthoic acid, and 2-hydroxycinnamate. Thus, this efflux system apparently has a high degree of specificity to certain aromatic carboxylic acids.

Example 5

Required Components of the yhcRQP Operon for the Efflux Function

The pHBA hypersensitivity of a yhcS regulatory mutant (shown in Example 3) allows a convenient assay for function of yhcRQP genes expressed from a multicopy plasmid. Thus, to define which components of this operon were necessary for the efflux function, the pHBA-sensitivity of strain DPD2433 ($yhcS^-$) carrying derivatives of pTrcHis2TOPO® that contained various inserted genes under control of the trc promoter was tested.

Plasmid pDEW673 contained the *E. coli* yhcQP genes under control of the trc promoter in a multicopy plasmid. To construct this plasmid, the yhcQP genes were obtained by PCR amplification using chromosomal DNA from *E. coli* strain MG1655 as template and the primers yhcP_left__928 (SEQ ID NO:8) and yhcQ_right (SEQ ID NO:9).

The yhcQ_right primer was designed so that when the amplified DNA was cloned into pTrcHis2TOPO® vector, an N-terminal fusion protein would not be formed and thus the native YhcQ protein was expressed. The yhcQ_right primer also had an EcoRI site that was used to determine orientation of the inserted DNA. The yhcP_left__928 primer was designed to contain the termination codon of yhcP and thus expressed the native YhcP protein, rather than a fusion protein. A 2922 bp product was obtained from amplification reactions using ExTaq™ (TaKaRa) and the following conditions: 94° C. for 5 minutes, 35 cycles of (94° C. for 1 minute, 60° C. for 2 minutes, 72° C. for 3 minutes), and 72° C. for 15 minutes. The product of the PCR reaction was used directly in a ligation with the pTrcHis2TOPO® vector (Invitrogen) following the protocol supplied by the vendor. After transformation of *E. coli* strain TOP10 (Invitrogen) and selection for Ampicillin resistance, plasmid DNA from individual transformants was digested with EcoRI. One plasmid, for which two fragments of sizes 4.4 kb (vector) and 2.9 kb (insert) resulted, was named pDEW673. The presence of the yhcQP genes in the correct orientation was confirmed by DNA sequence analysis of the ends of the insert DNA in pDEW673.

Plasmid pDEW675 contained the *E. coli* yhcRQ genes under control of the trc promoter in a multicopy plasmid. To construct this plasmid, the yhcRQ genes were obtained by PCR amplification using chromosomal DNA from *E. coli* strain MG1655 as template and the primers yhcQ_left (SEQ ID NO:10) and yhcR_right__928 (SEQ ID NO:11).

The yhcR_right__928 primer was designed so that when the amplified DNA was cloned into pTrcHis2TOPO® vector, an N-terminal fusion protein would not be formed and thus the native YhcR was expressed. The yhcR_right__928 primer also had an EcoRI site that was used to determine orientation of the inserted DNA. The yhcQ_left primer was designed to contain the termination codon of yhcQ and thus expressed the native YhcQ protein, rather than a fusion protein. A 1229 bp product was obtained from amplification reactions using ExTaq™ (TaKaRa) and the following conditions: 94° C. for 5 minutes, 35 cycles of (94° C. for 1 minute, 60° C. for 2 minutes, 72° C. for 3 minutes), and 72° C. for 15 minutes. The product of the PCR reaction was used directly in a ligation with the pTrcHis2TOPO® vector (Invitrogen) following the protocol supplied by the vendor. After transformation of *E. coli* strain TOP10 (Invitrogen) and selection for Ampicillin resistance, plasmid DNA from individual transformants was digested with EcoRI. One plasmid, for which two fragments of sizes 4.4 kb (vector) and 1.2 kb (insert) resulted, was named pDEW675. The presence of the yhcRQ genes in the correct orientation was confirmed by DNA sequence analysis of the ends of the insert DNA in pDEW675.

Plasmids pDEW668, pDEW673, pDEW675, and a control plasmid, pTrcHis2TOPO®/lacZ (Invitrogen), were moved by transformation to *E. coli* strain DPD2433, selecting for Ampicillin resistance, to generate strains DPD3317, DPD2455, DPD2457, and DPD3316, respectively. Table 8 below gives results for zone of growth inhibition (average of two experiments) resulting from the sodium salt of pHBA (80 μmoles/disk) on solidified Vogel-Bonner medium with 0.4% glucose as the carbon source.

TABLE 8 pHBA zone of growth inhibition results for *E. coli* strains

| Strain name | Host strain (Chromosomal mutation) | Plasmid (Genes expressed) | pHBA zone of growth inhibition, mm diameter |
|---|---|---|---|
| DPD3316 | DPD2433 ($yhcS^-$) | pTrcHis2TOPO ®/lacZ (lacZ control) | 23.5 clear |
| DPD3317 | DPD2433 ($yhcS^-$) | pDEW668 (yhcRQP) | 9.8 turbid |

TABLE 8-continued pHBA zone of growth inhibition results for *E. coli* strains

| Strain name | Host strain (Chromosomal mutation) | Plasmid (Genes expressed) | pHBA zone of growth inhibition, mm diameter |
|---|---|---|---|
| DPD2455 | DPD2433 (yhcS$^-$) | pDEW673 (yhcQP) | 9.5 turbid |
| DPD2457 | DPD2433 (yhcS$^-$) | pDEW675 (yhcRQ) | 17.0 slightly turbid |

These results show that multicopy expression of only yhcQ and yhcP is sufficient to fully reverse the pHBA sensitivity of the yhcS mutant and thus suggest that yhcR is not a required component of the efflux system. However, since a low level of expression of yhcR is possible in the yhcS strain, a role for yhcR cannot be entirely ruled out.

To test the requirement for yhcQ as a component of the efflux system, pDEW659, which contained the yhcP gene expressed from a tac promoter in vector pKK223-3, was used. To construct pDEW659, the yhcP gene was obtained by PCR amplification using chromosomal DNA from *E. coli* strain MG1655 as template and the primers YhcP-Left (SEQ ID NO:12) and YhcP-Right (SEQ ID NO:13).

The YhcP-Left primer was designed to contain a HindIII site and the YhcP-Right primer was designed to contain an EcoRI site for directional cloning of the resultant PCR product. A 1992 bp product was obtained from amplification reactions using ExTaq™ (TaKaRa) and the following conditions: 94° C. for 5 minutes, 30 cycles of (94° C. for 30 seconds, 55° C. for 30 seconds, 72° C. for 2 minutes), and 72° C. for 7 minutes. The product of the PCR reaction was digested with restriction enzymes EcoRI and HindIII. The restriction digestion also contained pKK223-3 at an approximate molar ratio of 2:1 (insert:vector). Following incubation at 37° C. for 1.5 hours, the enzymes were inactivated by incubation at 65° C. for 20 minutes. The enzymes were subsequently removed by use a Qiaquick PCR purification kit (Qiagen) according to the vendor's instructions. The purified restriction products were ligated using T4 DNA ligase at 16° C. overnight. Following ligation, PstI and SmaI digestions were used to linearize the vector without insert DNA. The DNA from this selection digestion was used for transformation of *E. coli* strain JM105 (Amersham Pharmacia Biotech Inc., Piscataway, N.J.) using selection for Ampicillin resistance. Plasmid DNA from individual transformants was digested with EcoRI and HindIII. One plasmid with a 2 kb inserted DNA was named pDEW659. This plasmid and others were placed in various host strains by transformation and selection for Ampicillin resistance. The pHBA zone of growth inhibition was tested, as above. The results are shown in Table 9.

TABLE 9 pHBA zone of growth inhibition results for *E. coli* strains

| Strain name | Host strain (Chromosomal mutation) | Plasmid (Genes expressed) | pHBA zone of growth inhibition, mm diameter |
|---|---|---|---|
| DPD2459 | MG1655 (+) | pKK223-3 (Control plasmid) | 10.0 turbid |
| DPD2466 | DPD2433 (yhcS$^-$) | pKK223-3 (Control plasmid) | 19.2 clear |
| DPD2467 | DPD2433 (yhcS$^-$) | pDEW659 (yhcP) | 18.8 clear |
| DPD2462 | DPD2444 (yhcP$^-$) | pKK223-3 (Control plasmid) | 22.8 clear |
| DPD2463 | DPD2444 (yhcP$^-$) | pDEW659 (yhcP) | 10.5 turbid |
| DPD2464 | DPD2444 (yhcP$^-$) | pDEW673 (yhcQP) | 9.8 turbid |
| DPD2465 | DPD2444 (yhcP$^-$) | pDEW675 (yhcRQ) | 21.8 clear |

These results show that multicopy expression of yhcP from plasmid pDEW659 was sufficient to reverse the pHBA-sensitivity of the yhcP mutant strain and thus proving that yhcP was expressed from this plasmid. However, multicopy expression of yhcP from plasmid pDEW659 was not sufficient to reverse the pHBA sensitivity of the yhcS mutant. Thus, yhcQ is required for function of the efflux system. Note also that the hypersensitivity of the yhcP mutant strain demonstrates that yhcP requirement for efflux function.

Thus, we conclude that the products of both yhcP and yhcQ are necessary for function of this aromatic carboxylic acid efflux system, but that the product of yhcR is not likely to be required.

Example 6

Genetic Evidence that the to/C-Encoded Outermembrane Factor is not Required for Efflux Function of yhcQP Many efflux pumps in *E. coli* and other gram-negative bacteria consist of a tripartite system. An inner membrane protein, which is the efflux transporter, often works with a periplasmic protein from the "Membrane Fusion Protein Family" and an outermembrane protein from the "Outermembrane Factor Family". Since YhcQ is a member of the "Membrane Fusion Protein Family", it may be expected that this efflux system would function with a member of the "Outermembrane Factor Family". In *E. coli* tolC encodes an "Outermembrane Factor Family" member that has been shown to work with several different efflux systems. Thus, TolC is a possible candidate for functioning with YhcP and YhcQ to provide efflux of aromatic carboxylic acids. However, genetic experiments described below do not support a role for TolC function with YhcP and YhcQ.

These genetic results were obtained by testing the pHBA sensitivity of each of a series of mutant *E. coli* strains. Strain DPD1818 carries a to/C::miniTn10 mutation in the MG1655 background. It was constructed by transduction of *E. coli* MG1655 using P1clr100 Cm phage grown on *E. coli* strain DE112 (Van Dyk et al. *Appl. Environ. Microbiol.* 60:1414-1420 (1994)), which carries a tolC::miniTn10 mutation, and selection for tetracycline resistance. Strain DPD2444, described above, carries a yhcP::TN<Kan> mutation. Strain DP2446 carries both the tolC::miniTn10 and yhcP::TN<Kan>. This strain was constructed using by P1clr100Cm mediated transduction of DE112 with phage grown on strain DPD2443 and selection for kanamycin resistance. Each of these mutant strains was grown overnight in LB medium at 37° C. The overnight cultures were used to inoculate LB medium containing various concentrations of the sodium salt of pHBA. The final volume in the wells of a 96-well microplate was 100 μl and the final dilution of the inoculum was 1 to 1000. This microplate was covered and incubated at 37° C. for 7 hours and then incubated at room temperature for 3 days. The growth in each well was then scored visually. The results are shown in Table 10.

TABLE 10

Growth of *E. coli* strains in the presence of pHBA

| *E. coli* strain | Genotype | Growth in LB medium for 3 days at room temperature with and without pHBA 0 mM | 25 mM | 50 mM | 100 mM | 200 mM |
|---|---|---|---|---|---|---|
| MG1655 | + | ++++ | ++++ | ++++ | +++ | − |
| DPD1818 | tolC | ++++ | ++++ | ++++ | + | − |
| DPD2444 | yhcp | ++++ | ++++ | ++++ | − | − |
| DPD2446 | tolC yhcP | ++++ | ++++ | + | − | − |

++++ indicates full turbidity
+++ indicates moderate, but visually less than full turbidity
+ indicates very slight turbidity
− indicates no turbidity The tolC mutation alone conferred hypersensitivity to pHBA. This is consistent with the presence of one or more pHBA efflux pumps in *E. coli* that utilizes the TolC channel. If YhcP/YhcQ efflux system required TolC for function, it would be expected that the pHBA sensitivity of the tolC mutant strain would be equal to or greater than that of the yhcP mutant. Furthermore, no additivity of the two mutants would be expected. An illustrative example of this genetic principle of epistasis of mutations in components of the same system is provided by the AcrA/AcrB efflux pump, which is known to utilize the TolC channel. *E. coli* strains carrying mutations in acrA are hypersensitive to sodium dodecyl sulfate and novobiocin, while a tolC mutant strain has a greater degree of sensitivity than the acrA mutant strain. The strain carrying mutations in both acrA and tolC has sensitivity equivalent to the tolC single mutant. In contrast, the degree of pHBA hypersensitivity conferred by the yhcP mutation is somewhat greater than that conferred by the tolC mutation and the double mutant of tolC and yhcP is more sensitive than either mutant alone. Thus, these results suggest that the YhcP efflux pump does not require exclusive use of TolC.

An additional experiment is consistent with the above conclusion. This experiment used *E. coli* strain MG1655 and strains derived from it, DPD1818 (described above in this example) with a to/C::miniTn10 mutation, DPD4233 (described in example 3) with a yhcS::TN<Kan> mutation, and DPD2435 that carries both the to/C::miniTn10 and yhcS::TN<Kan> mutations. The latter strain was constructed using P1clr100Cm mediated transduction of DE112 with phage grown on strain DPD2410 (described in Example 3) and selection for kanamycin resistance. These four strains were each transformed with plasmids pTrcHis2TOPO®/lacZ (Invitrogen) for a control and pDEW668 that expresses the yhcRQP operon (described in Example 2). The MIC for pHBA was determined by visually assessing growth in 100 µl volume in microplates after incubation for 21 hours at 37° C. Vogel-Bonner minimal medium with 0.4% glucose was used. The sodium salt of pHBA was added to 100 mM final concentration and a series of 3:4 dilutions of pHBA were tested. The inoculum was 50 µl of a 1:500 dilution into Vogel-Bonner medium with 0.4% glucose as a carbon source of overnight cultures of each of the plasmid-containing strains grown in the same medium except with addition of 25 µg/ml Ampicillin. Table 11 shows the MICs for pHBA defined as the lowest concentration where no growth was visible.

TABLE 11 pHBA MICs for *E. coli* strains

| Plasmid | Host Stain (genotype) MG1655 (+) | DPD2433 (yhcS$^-$) | DPD1818 (tolC$^-$) | DPD2435 (yhcS$^-$, tolC−) |
|---|---|---|---|---|
| pTrcHis2TOPO ®/lacZ (control) | 100 mM | 18 mM | 56 mM | 13 mM |
| pDEW668 (yhcRQP) | 100 mM | 100 mM | 100 mM | 100 mM |

Comparing the sensitivity of the strains carrying the control plasmid, the double yhcS and tolC mutant was more sensitive to pHBA than either single mutant. This result is consistent with independent function of TolC and the YhcQP efflux system, the expression of which requires YhcS function. Furthermore, the plasmid expressing yhcRQP conferred full pHBA resistance in the tolC mutant host strains. This result also suggests that TolC is not required for YhcQP efflux pump function.

Overall, these results can be interpreted as consistent with the presence of at least two pHBA efflux systems in *E. coli*, one that uses TolC and the YhcP/YhcQ system that does not. Hence, a distinctive of the YhcP/YhcQ efflux system is accented by its difference from many efflux pumps in *E. coli* that use the TolC channel-tunnel.

At present, it is not known if one of the other putative outermembrane factor family members present in the *E. coli* genome, CusC, YohG, or YjcP, works with the YhcP/YhcQ efflux system. Alternatively this efflux system may use another type of outermembrane protein for efflux or may not require an outermembrane component.

Example 7

Multicopy Expression of yhcRQP Allows Cell Growth at Conditions that are Otherwise Bactericidal The plasmid pDEW668 (described in Example 2) that carries the *E. coli* yhcRQP pHCA efflux system was moved by transformation into *E. coli* strain MG1655 obtained from the American Type Culture Collection, Manassas, Va. (ATCC #700926. lot # 2660700) to form strain DPD4057. For a control, plasmid pTrcHis2TOPO®/lacZ was also put into the same host strain, making strain DPD4055. *E. coli* strains DPD4055 and DPD4057 were grown overnight at 37° C. in a defined medium made with 4 g/l $(NH_4)_2SO_4$, 1.26 g/l $KH_2PO_4$, 2.42 g/l $K_2HPO_4$, 0.5 g/l $MgSO_4.7H_2O$, 30 mM MOPSO, pH 7.0, 1 mg/l thiamin, 50 mg/l citric acid, 7.5 mg/l $CaCl_2.2H_2O$, 25 mg/l $FeSO_4.7H_2O$, 1.95 mg/l $ZnSO_4.7H_2O$, 1.9 mg/l $CuSO_4.5H_2O$, 1.0 mg/l $CoCl_2.6H_2O$, 1.5 mg/l $MnCl_2.4H_2O$, 7.5 g/l glucose, and 25 µg/ml ampicillin. The next day, tubes with 1.0 ml of the same medium containing 7.5, 5.0, 3.3, 2.2, 1.5, or 0 g/l pHCA were inoculated with 10 µl of the overnight cultures. These tubes were grown at 37° C. on a roller drum in the dark for 1 to 2 days. At 21 hours after inoculation, the tube with 5.0 g/l pHCA inoculated with DPD4057 had visible growth. In contrast, strain DPD4055 had visible growth at 2.2 g/l pHCA, but not higher. Thus, a 2.3 fold improvement in pHCA tolerance by multicopy expression of yhcRQP was observed at these conditions.

At 48 hours of incubation, the CFU/ml of the cultures growing in the presence of 7.5 g/l pHCA was determined by plating dilutions onto LB plates. Strain DPD4055 had $2\times10^2$ CFU/ml. Strain DPD4057 had $8\times10^7$ CFU/ml. The inoculum for each culture was $2\times10^7$ CFU/ml. Thus, 7.5 g/l pHCA had a bactericidal effect on the strain without the multicopy yhcRQP genes. In contrast, the culture carrying multicopy yhcRQP increased in CFU/ml. This result reemphasizes the critical role that this efflux system plays in pHCA tolerance.

We claim:

1. A method for increasing the resistance of a host cell to aromatic carboxylic acids comprising:
   a) providing a host cell which comprises at least one first polynucleotide having a sequence as set forth in SEQ ID NO:2 and at least one second polynucleotide having a sequence as set forth in SEQ ID NO:1; and
   b) up-regulating the expression of the at least one first and second polynucleotides of (a) whereby the host cell resistance to aromatic carboxylic acids is increased as compared with an unmodified host cell.

2. A method according to claim 1 wherein the at least one first and second polynucleotides are endogenous to said host cell.

3. A method according to claim 1 wherein the at least one first and second polynucleotides are heterologous to said host cell.

4. A method according to claim 1 wherein the host cell is selected from the group consisting of bacteria, yeast, fungi and plants.

5. A method according to claim 4 wherein the host cell is an enteric bacteria.

6. A method according to claim 4 wherein the host cell is selected from the group of genera consisting of *Escherichia, Salmonella, Bacillus, Acinetobacter, Streptomyces, Methylobacter, Rhodococcus, Corynebacterium, Pseudomonas, Rhodobacter*, and *Synechocystis*.

7. A method according to claim 1 wherein the aromatic carboxylic acid is selected from the group consisting of of para-hydroxybenzoic acid, para-hydroxycinnamic acid, cinnamic acid, salicylic acid, benzoic acid, and 1-napthoic acid.

8. A method according to claim 1 wherein the at least one first and second polynucleotides are expressed on a multi-copy plasmid.

9. A method according to claim 1 wherein the at least one first and second polynucleotides are under the control of a strong promoter selected from the group consisting of lac, trp, $lP_L$, $lP_R$, T7, tac, and trc.

* * * * *